(12) United States Patent
Molz, IV et al.

(10) Patent No.: US 7,553,320 B2
(45) Date of Patent: Jun. 30, 2009

(54) METHOD AND APPARATUS FOR REPLACING THE FUNCTION OF FACET JOINTS

(75) Inventors: Fred Molz, IV, Collierville, TN (US); Jeff Justis, Collierville, TN (US); Michael Sherman, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 417 days.

(21) Appl. No.: 10/733,554

(22) Filed: Dec. 10, 2003

(65) Prior Publication Data

US 2005/0131405 A1  Jun. 16, 2005

(51) Int. Cl.
*A61B 17/70* (2006.01)
(52) U.S. Cl. .................... 606/247; 623/17.11
(58) Field of Classification Search .......... 606/61, 606/246–247, 248–279, 76, 900, 907, 910–911; 623/17.11–17.16; 403/11
See application file for complete search history.

(56) References Cited

U.S. PATENT DOCUMENTS

| | | | |
|---|---|---|---|
| 2,235,488 A | | 3/1941 | Mercier |
| 3,648,691 A | * | 3/1972 | Lumb et al. .................. 606/61 |
| 5,415,661 A | * | 5/1995 | Holmes ........................ 606/69 |
| 5,425,773 A | * | 6/1995 | Boyd et al. ............... 623/17.15 |
| 5,456,722 A | * | 10/1995 | McLeod et al. ............. 128/898 |
| 5,733,284 A | * | 3/1998 | Martin ........................ 606/61 |
| 5,961,516 A | | 10/1999 | Graf |
| RE36,758 E | * | 6/2000 | Fitz ........................ 623/17.11 |
| 6,238,396 B1 | * | 5/2001 | Lombardo .................... 606/61 |
| 6,267,764 B1 | * | 7/2001 | Elberg ......................... 606/61 |
| 6,402,750 B1 | * | 6/2002 | Atkinson et al. ............. 606/61 |
| 6,419,703 B1 | | 7/2002 | Fallin et al. |
| 6,440,169 B1 | * | 8/2002 | Elberg et al. ............. 623/17.16 |
| 6,652,527 B2 | * | 11/2003 | Zucherman et al. .......... 606/61 |
| 2002/0065557 A1 | | 5/2002 | Goble et al. |
| 2002/0072800 A1 | | 6/2002 | Goble et al. |
| 2002/0095154 A1 | | 7/2002 | Atkinson et al. |
| 2003/0220643 A1 | * | 11/2003 | Ferree ......................... 606/61 |
| 2005/0101956 A1 | * | 5/2005 | Simonson .................... 606/61 |

FOREIGN PATENT DOCUMENTS

| | | |
|---|---|---|
| SU | 848 009 | 7/1981 |
| WO | WO 01/45576 | 6/2001 |
| WO | WO 2004/098423 | 11/2004 |

OTHER PUBLICATIONS

Patent Cooperation Treaty—European Patent Office, "Notification of Transmittal of The International Search Report and The Written Opinion of the International Searching Authority, or the Declaration," Jun. 2, 2005, 20 pages.

* cited by examiner

*Primary Examiner*—Eduardo C Robert
*Assistant Examiner*—James L Swiger

(57) ABSTRACT

A system and method is provided for replacing the functions of a facet joint between a superior vertebra and an inferior vertebra without necessarily requiring an anatomical implant. The method includes: providing one or more flexible posterior devices to replace main functions of the facet joint; and adapting a first one of the one or more posterior devices for a first attachment to a first pedicle, and a second attachment to a second pedicle.

15 Claims, 4 Drawing Sheets

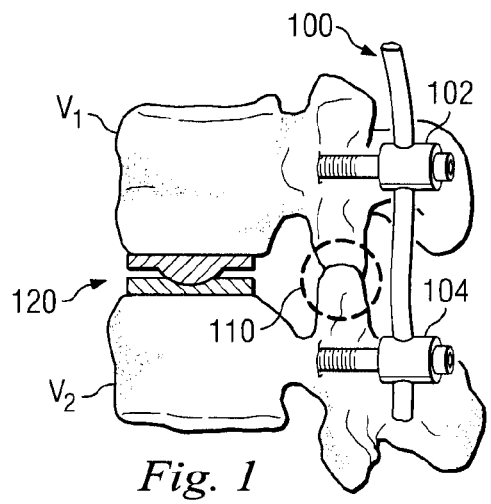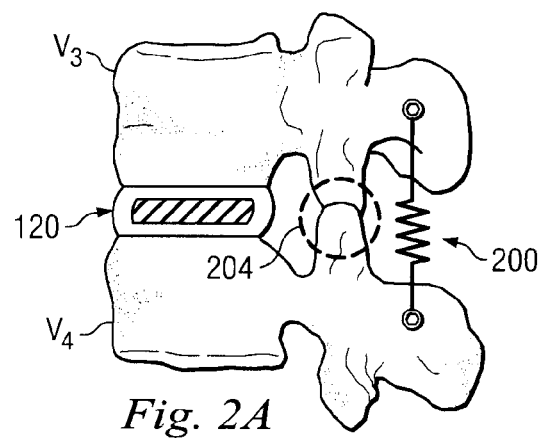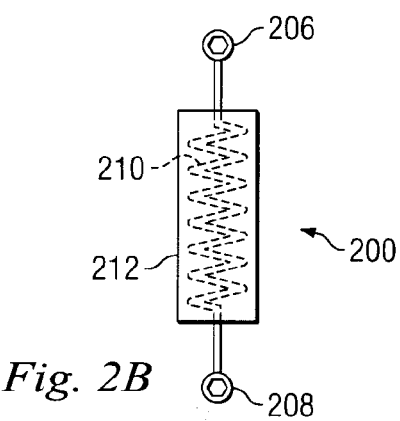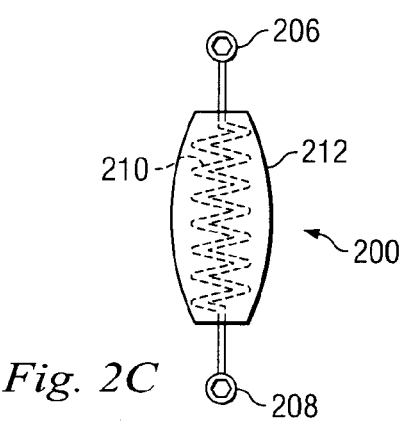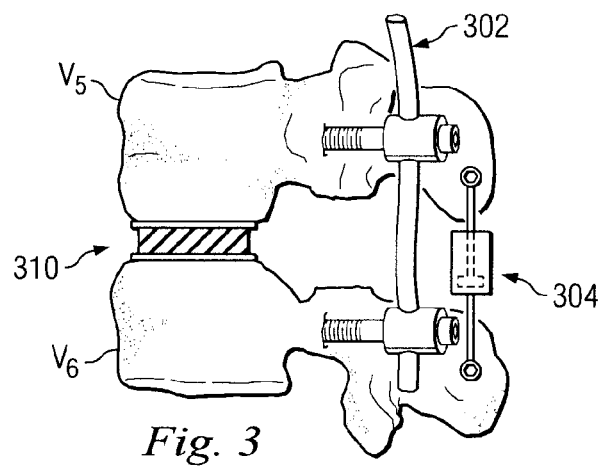

METHOD AND APPARATUS FOR REPLACING THE FUNCTION OF FACET JOINTS

FIELD OF THE INVENTION

The present disclosure relates to spinal devices and methods, and more particularly, to a system and method for replacing the functions of a facet joint between a superior vertebra and an inferior vertebra without necessarily requiring an anatomical implant.

Background

A vertebrae includes a vertebral body and posteriorly extending structures including pedicles, a lamina, articular processes, and a spinous process. The articular processes include superior and inferior processes that join to form zygapophyseal, or facet joints, with adjacent vertebrae. The facet joints are formed by the articular processes of adjacent vertebrae—the inferior articular process of a vertebra articulates with the superior articular process of the vertebra below. Facet joints perform several functions, including stabilizing the spine and carring approximately 20% of the compressive load on the spine. Accordingly, their anatomic position and orientation affect the mobility of each spinal region. For example, in the cervical region, facet joints are oriented in the coronal plane and are capable of a significant range of motions in the six degrees of freedom. In the lumber area, facet joints are oriented parasagittal and thereby limit rotation.

Major trauma or repetitive minor trauma may cause a facet joint to be damaged or otherwise degenerate. As a result, the hyaline cartilage that lines the joint can lose its water content, and eventually become worn. When this happens, the articular processes begin to override each other as the joint capsules become stretched, resulting in the malalignment of the joints and abnormal biomechanical function of the motion segment.

The current treatment for degenerated or otherwise damaged facet joints is to provide prosthetic facet joints. The prosthetic facet joints are shaped and positioned similar to the original facet joint, and must be constructed to withstand the required movement and weight handling functions of the original facet joint. Such requirements are difficult to achieve while also meeting requirements of reliability and durability. What is needed is a system and method for reducing and/or eliminating the need for anatomical prosthetic facet joints.

Summary

The present invention provides a system and method for replacing the functions of a facet joint between a superior vertebra and an inferior vertebra without necessarily requiring an anatomical implant.

In one embodiment, a surgical implant for replacing functions of a facet joint between adjacent vertebrae is provided. The surgical implant includes a first biocompatible attachment device for attaching to a first pedicle of a superior vertebrae and a second biocompatible attachment device for attaching to a second pedicle of an inferior vertebrae. The surgical implant also includes a flexible member attached to the first and second biocompatible attachment devices. The first and second biocompatible attachment devices are positioned, and the flexible member is adapted, so that the surgical implant applies a distracting force between the superior and inferior vertebrae sufficient for selectively maintaining the first and second pedicles at a predetermined distance.

In another embodiment, a facet replacement system is provided. The facet replacement system includes a first posterior device having first and second attachment mechanisms and a compression-resistant member connected there between, and a second posterior device having first and second attachment mechanisms and an expansion-resistant member connected there between. The first attachment mechanisms are adapted to connect to respective portions of a superior spinous process, and the second attachment mechanisms are adapted to connect to respective portions of an inferior spinous process.

In another embodiment, a method for replacing functions of a facet joint between adjacent vertebrae is provided. The method includes: providing one or more flexible posterior devices to replace main functions of the facet joint; and adapting a first one of the one or more posterior devices for a first attachment to a first pedicle, and a second attachment to a second pedicle.

In another embodiment, a prosthetic device for replacing functions of a facet joint between adjacent vertebrae comprises: means for providing one or more flexible posterior devices to replace main functions of the facet joint; and means for adapting a first one of the one or more posterior devices for a first attachment to a first transverse process, and a second attachment to a second transverse process.

In another embodiment, a method for replacing functions of a facet joint between adjacent vertebrae comprises: providing one or more flexible posterior devices to replace main functions of the facet joint; and adapting a first one of the one or more posterior devices for a first attachment to a first articular process, and a second attachment to a second articular process.

In another embodiment, a method for replacing functions of a facet joint between adjacent vertebrae comprises: providing one or more flexible posterior devices to replace main functions of the facet joint; and adapting a first one of the one or more posterior devices for a first attachment to a first spinous process, and a second attachment to a second spinous process.

In another embodiment, a method for replacing functions of a facet joint between adjacent vertebrae comprises: providing one or more flexible posterior devices to replace main functions of the facet joint; and adapting a first one of the one or more posterior devices for a first attachment to a first lamina, and a second attachment to a second lamina.

In another embodiment, a method for replacing functions of a facet joint between adjacent vertebrae comprises: attaching one or more posterior devices to the adjacent vertebrae to replace main functions of the facet joint without utilizing any anatomical facet joint implant.

In another embodiment, a posterior device for replacing functions of a facet joint comprises: a first component comprising an elongated body; and a first joint having a first opening wherein the first opening contains an elastic material; a second component comprising: an elongated body; and a second joint having a second opening wherein the second joint is coupled with the first joint, and the second opening contains the elastic material; and a connector covering the first joint and the second joint wherein the connector comprises the elastic material.

BRIEF DESCRIPTION OF THE DRAWINGS

FIG. 1 illustrates a posterior device and an anterior device for replacing functions of a facet joint according to one embodiment of the present invention.

FIG. 2A illustrates a posterior device and an anterior device for replacing functions of a facet joint according to one embodiment of the present invention.

FIGS. 2B and 2C illustrates exemplary posterior devices.

FIG. 3 illustrates posterior devices and an anterior device for replacing functions of a facet joint according to one embodiment of the present invention.

DETAILED DESCRIPTION

Figure 4:
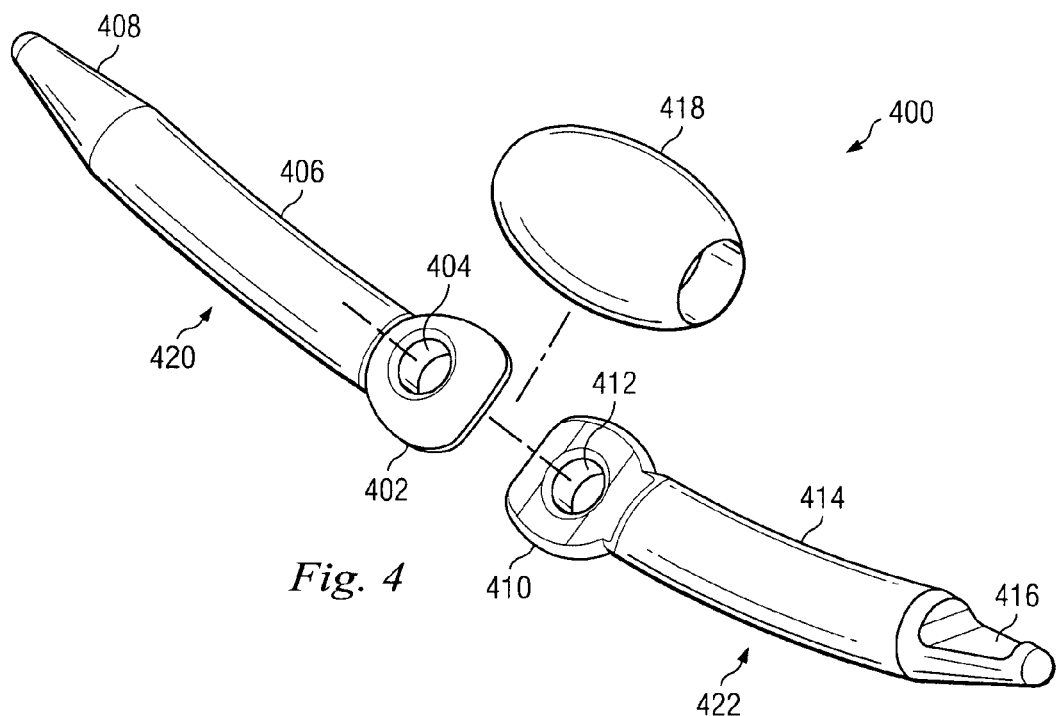
FIG. 4 illustrates components of a posterior device for replacing functions of a facet joint according to one embodiment of the present invention.

For the purposes of promoting an understanding of the principles of the invention, references will now be made to the embodiments, or examples, illustrated in the drawings, and specific languages will be used to describe the same. It will nevertheless be understood that no limitation of the scope of the invention is thereby intended. Furthermore, reference numerals are repeated for the sake of simplicity, and do not, by themselves, designate any combination of elements discussed in the different embodiments. Any alterations and further modifications in the described embodiments, and any further applications of the principles of the invention as described herein are contemplated as would normally occur to one skilled in the art to which the invention relates.

Referring now to FIG. 1, for the sake of example, two adjacent vertebrae V1 and V2 are shown with a damaged or degenerated facet joint 110. The present embodiment attempts to replicate the functions (or some functions) of the facet joint 110 without necessarily requiring an anatomical implant such as a prosthetic facet joint device. It is understood, however, that an anatomical implant can still be used in some embodiments, as desired. To replace the functions of the facet joint 110, a posterior device 100 and/or an anterior device 120 are utilized. The posterior device 100 may be utilized alone or may be combined with the anterior device 120 to replicate the functions of the facet joint 110. Conversely, a stand along anterior device (without a posterior device) could be used to replicate the functions of the facet joint.

To implement the functions of the facet joint 110 in the posterior device 100 and/or the anterior device 120, many methods may be employed to evaluate the functional requirements of the facet joint 110. For example, the spinal load carried by the facet joint 110 can be determined. Alternatively or in addition, motion analysis methods, which utilize design devices to reproduce the motions of the facet joint 110, may be utilized.

Once the functional requirements of the facet joint 110 are evaluated, the composition of the posterior device 100 may be selected to meet these requirements. Examples include flexible biocompatible devices, such as devices constructed of shape memory alloys, cables, or springs. In the illustration of FIG. 1, the posterior device 100 is a flexible cable. In the present embodiment, the posterior device 100 may reside in a variety of physical locations, so that the device can be sized to meet the functional requirements instead of meeting the space and shape requirements of the facet joint 110. In this illustration of FIG. 1, the posterior device 100 is attached to the pedicles of the vertebrae V1 and V2 by biocompatible attachment devices 102 and 104, such as pedicle screws. Other examples of attachment devices include staples, rivets, and locking grooves formed within the vertebrae for receiving a securing portion of the device 100. It is contemplated that the posterior device 100 may also be attached to other parts of the vertebrae V1 and V2, such as articular processes, transverse processes, spinous processes, or laminae. It is further contemplated that tethers, staples, and other anchoring devices can be used.

The posterior device 100 may be a flexible cable that is made of shape memory materials, which may be polymer-based or Nitinol. For example, the posterior device 100 may comprise approximately half Ni and half Ti, and may be treated in hot air and then cold water to produce an austenite finish temperature that is lower than the temperature range of a human body. In this example, the posterior device 100 may have an austenite finish temperature of approximately 34° C. Accordingly, at above 34° C., the posterior device 100 becomes superelastic.

Prior to implanting the posterior device 100 into a human body, it may be cooled to below 34° C. to maintain a predefined shape for easy insertion. Alternatively, it may remain at a temperature of above 34° C., so that its superelasticity may assist the insertion.

The anterior device 120 may be inserted into a disc space between the vertebrae V1 and V2. In the illustration of FIG. 1, the anterior device 120 is a disc replacement device, such as disclosed in U.S. Pat. No. 6,402,785 (assigned to SDGI Holdings, Inc., and hereby incorporated by reference). Other examples of anterior devices 120 include flexible biocompatible devices, such as a cable, a spring, or a device made of shape memory alloys.

Depending on the condition of the facet joint 110, it may or may not be surgically removed. For example, if the facet joint 110 causes severe pain, then it may warrant removal. Alternatively, the facet joint 110 may be left in place and may even be utilized to a limited extent.

Referring now to FIG. 2A, in another embodiment, a facet joint 204 between vertebra V3 and V4 may be damaged or degenerated. As a result, a posterior device 200, which may be used alone, or combined with an anterior device 202, may replace the functions (or main functions) of the facet joint 204.

Referring now to FIG. 2B, in one embodiment, the posterior device 200 may be a biocompatible spring that includes a pair of attachment devices 206 and 208, a bias member 210, and a housing attachment 212.

The attachment devices 206 and 208 may comprises any conventional attachment device, such as pins, connectors, cotters, rivets, spikes, keys, couplings, or bushings. In this illustration, the attachment devices 206 and 208 are biocompatible screws that may be inserted into the vertebrae V3 and V4 to secure the posterior device 200.

The bias member 210 may reshape in response to spinal motions. Similar to the function of a conventional spring, the bias member 210 responds to spinal movements by replicating the functions of the facet joint 204. For example, the bias member 210 may be compressed as a load is imposed upon the spine, but become extended during a flexion motion. It is contemplated that the bias member 210 may operate within its elastic range as determined by its chosen material and structure. It is further contemplated that the bias member 210 may comprise any biocompatible material, such as titanium, carbon fiber, polymers, or shape memory alloys.

The housing attachment 212 may be used to protect the bias member 210 from the interference of surrounding tissues, so that the tissues will not inadvertently clog the bias member 210 and impede its proper function. It is contemplated that the housing attachment 212 may comprise any biocompatible material, such as rubber or shape memory alloys.

It is contemplated that the posterior device 200 and its components may comprise a variety of shapes, such as the one illustrated in FIG. 2C. It is further contemplated that the posterior device 200 may include a plurality of bias members, or that may simply be a conventional spring. It is also contemplated that the posterior device 200 may be any flexible biocompatible device, such as a cable, or a device made of shape memory alloys.

The posterior device 200 may be attached to the transverse processes of the vertebrae V3 and V4 by any conventional biocompatible attachment devices, such as pins, connectors, cotters, rivets, spikes, keys, couplings, bushings, washers, or other anchoring devices. It is also contemplated that the posterior device 200 may be attached to pedicles, articular processes, spinous processes, or laminae of the veterbrae V3 and V4.

The anterior device 202, which may be a nucleus device, may be inserted into a disc space between the vertebrae V3 and V4, and work together with the posterior device 200 to replace the functions of the facet joint 204. The anterior device 202 may comprise any conventional nucleus replacement devices. Alternatively, it may comprise any flexible biocompatible device, such as a cable, a spring, or a device made of shape memory alloys. It will be understood that conventional nucleus replacement devices are known in the art, and will not be described further herein.

Depending on the condition of the disc joint 204, it may or may not be surgically removed. For example, if the disc joint 204 causes severe pain, it may be surgically removed. Alternatively, without substantially relying on its functions, it may be left in the animal body.

Referring now to FIG. 3, in yet another embodiment, a combination of a posterior device 302 and a posterior device 304 may be used to replace the functions (or main functions) of a damaged facet joint (not shown) between vertebrae V5 and V6. It is also contemplated that an anterior device 310, which may be similar to previously described devices 108 or 202, may function together with the posterior devices 302 and 304 to replace the facet joint functions.

The posterior device 302 and the posterior device 304 may compliment each other in replicating the functions of the facet joint. For example, the posterior device 302 may be a biocompatible spring that regulates the capacity of the replaced facet joint functions, while the posterior device 304 may be a damper that regulates the movement of the replaced facet joint functions. The posterior device 302 may be any of the previously described posterior device 100 or 200, or a biocompatible damper. Likewise, the posterior device 304 may be any of the previously described posterior device 100 or 200. In one example, the posterior device 304 may be a damper identical or similar to the embodiments disclosed in the U.S. Pat. No. 2,235,488 entitled "Shock-Absorbing Device", which is hereby incorporated by reference.

In this example, the posterior device 302 is attached to pedicles via pedicle screws, while the posterior device 304 is attached to transverse processes of the vertebrae V5 and V6. Alternatively, each of the posterior devices 302 and 304 may be attached to any of articular processes, transverse processes, spinous processes, laminae, or pedicles of the vertebrae V5 and V6. It is contemplated that one or more additional posterior devices may be added to the posterior devices 302 and 304, and all of them may work together to replace the facet joint functions.

Even though previous embodiments are directed toward replacing the functions of a single facet joint, it is contemplated that this invention may be applied to replace the functions of a plurality of facet joints. For example, a bilateral approach may be adopted to replace damaged facet joints on both sides of a disc.

Referring now to FIG. 4, in another embodiment, a posterior device 400 may comprise a connector 418, a first component 420, and an second component 422. The posterior device 400 may be used alone, or in combination with one or more additional posterior and/or anterior devices described previously, to replace the functions of a facet joint without any anatomical facet joint implant. It is contemplated that the posterior device 400 may be used to replace any of the posterior devices 100, 200, 302 or 304 in the previously described embodiments.

The connector 418 provides elasticity for the posterior device 400 to allow motions that imitate the functions of a facet joint. The connector 418 may comprise any elastic biocompatible material, such as rubber, silicon or shape memory alloys. It may comprise any suitable shape, which may be a hollowed olive or a partial sphere.

The first component 420 may comprise a tip 408, an elongated body 406, which may be a rod or shaft, and a joint 402. The tip 408 may be pointed, and adapted for a percutaneous insertion of the posterior device 400, which may entail pushing the posterior device 400 through tissues of an animal body. The joint 402 comprises an opening 404, which may contain any biocompatible elastic material, such as rubber, silicon or shape memory alloys, to facilitate motions of the posterior device 400.

The second component 422 may have an identical or similar structure as that of the first component 420. In this illustration, the second component 422 may comprise a tip 416, an elongated body 414, which may be a rod or shaft, and a joint 410. The tip 416 may be pointed, and adapted for a percutaneous insertion of the posterior device 400, which may entail pushing the posterior device 400 through tissues of an animal body. The joint 410 comprises an opening 412, which may contain any biocompatible elastic material, such as rubber, silicon or shape memory alloys, to facilitate motions of the posterior device 400. The opening 412 may be coupled to the opening 404, so that an elastic material may flow through both openings 404 and 412 to facilitate the functions of the posterior device 400. It is also contemplated that the second component 422 may have a different structure from that of the first component 420.

The first and second components 420 and 422 may be coupled together by any conventional means, such as being molded or screwed together through their respective joints 402 and 410, to form a unit. Further, they may be coupled at different angles to simulate the natural anatomy of facet joints. For example, to replace functions of a facet joint in the cervical region, the first and second components 420 and 422 may be coupled at approximately 45° to the horizon to simulate the orientation of a natural facet joint. In another example, to replace functions of a facet joint in the thoracic region, the first and second components 420 and 422 may be coupled at an angle of approximately 60° to the axial plane and 20° to the frontal plane of a human body. In the lumbar area, the first and second components 420 and 422 may be joined at an angle of approximately 90° to the axial plane and 45° to the frontal plane of a human body.

Each of the first and second components 420 and 422 may comprise any biocompatible material, such as stainless steel, titanium, shape memory alloys, polymers, carbon fiber, and porous material. It is contemplated that the posterior device 400 may be attached to any of the pedicles, articular processes, transverse processes, spinous processes, or laminae of vertebrae.

Figure 5:
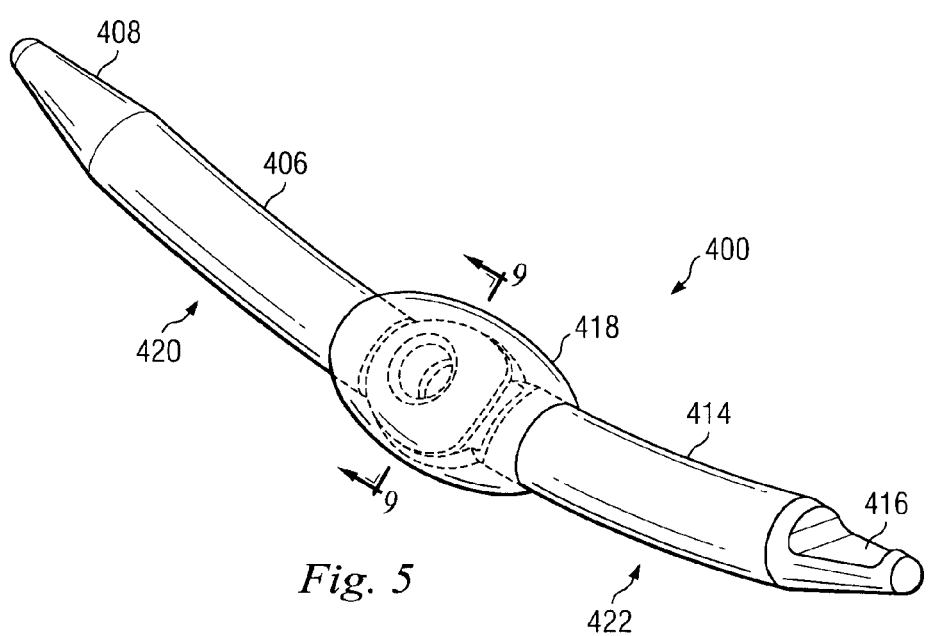
FIG. 5 illustrates an assembled posterior device of FIG. 4.

Referring now to FIG. 5, the posterior device 400 may be inserted into the spinal region as a unit by any conventional approach, such as a posterior or lateral approach. It is also contemplated that the posterior device 400 may be inserted into the spinal region by the approaches disclosed in the U.S. Pat. No. 6,530,929 (assigned to SDGI Holdings, Inc.).

Utilization of the posterior devices 100, 200, 302, 304, and 400 will now be described. The posterior device(s) may be inserted into the spinal region by any conventional approach, such as a posterior or lateral approach. For example, procedures and instruments useable in a posterior approach are disclosed in U.S. Pat. No. 6,241,729 (assigned to SDGI Holdings, Inc.), and a publication by Sofamor Danek ©1996 entitled "Surgical Technique using Bone Dowel Instrumentation for Posterior Approach", each of which is incorporated herein by reference in its entirety. It is also contemplated that any of the posterior devices 100, 200, 302, 304, and 400 may be inserted into the spinal region by the approaches disclosed in the U.S. Pat. No. 6,530,929 (assigned to SDGI Holdings, Inc., and hereby incorporated by reference).

The anterior devices 120, 202 and 303 may be inserted into the spinal region by any conventional approach, such as an anterior, a posterior or lateral approach. For example, procedures and instruments useable in an anterior approach are disclosed in U.S. Pat. No. 6,428,541 (assigned to SDGI Holdings, Inc.), and the publication by Sofamor Danek© 1996 entitled "Surgical Technique using Bone Dowel Instrumentation for Anterior Approach", each of which is incorporated herein by reference in its entirety.

Figure 6:
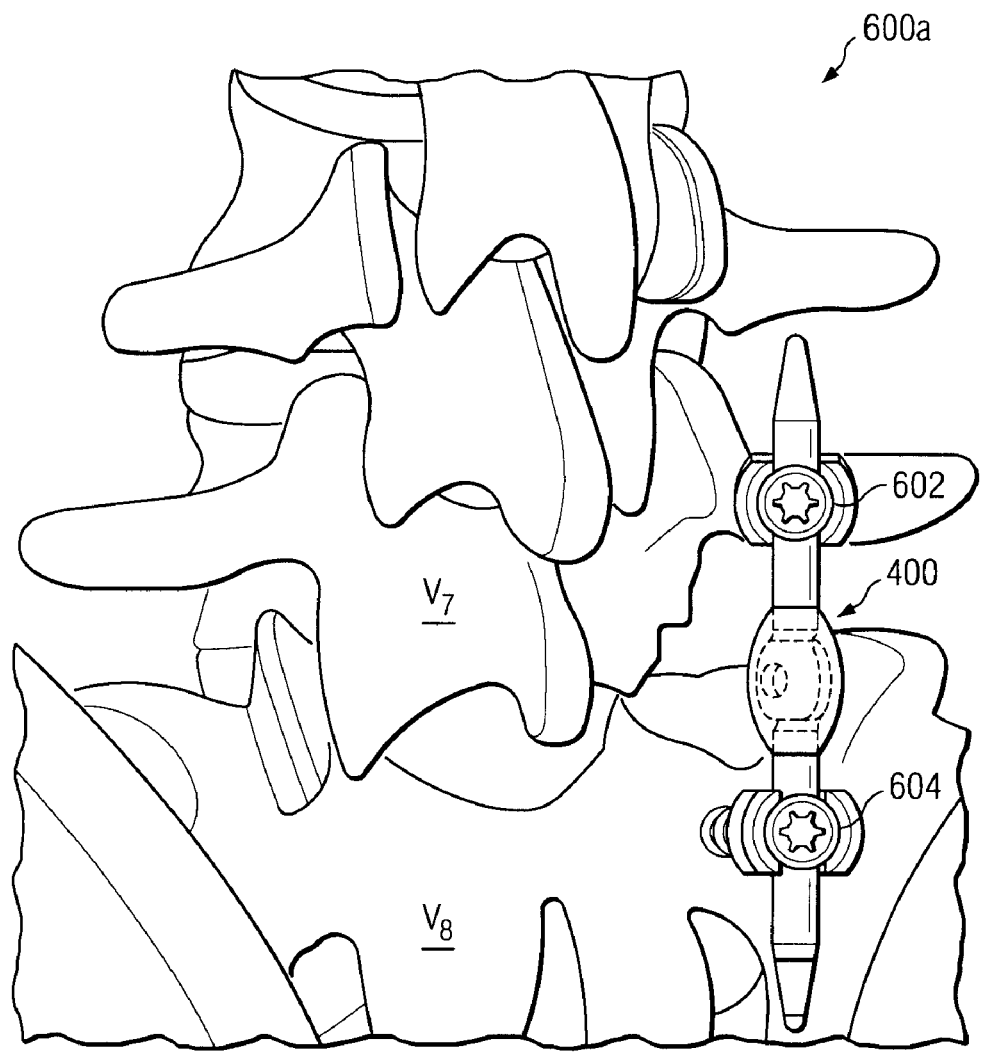
FIGS. 6-8 illustrate exemplary usages of the posterior device of FIG. 5.
Figure 7:
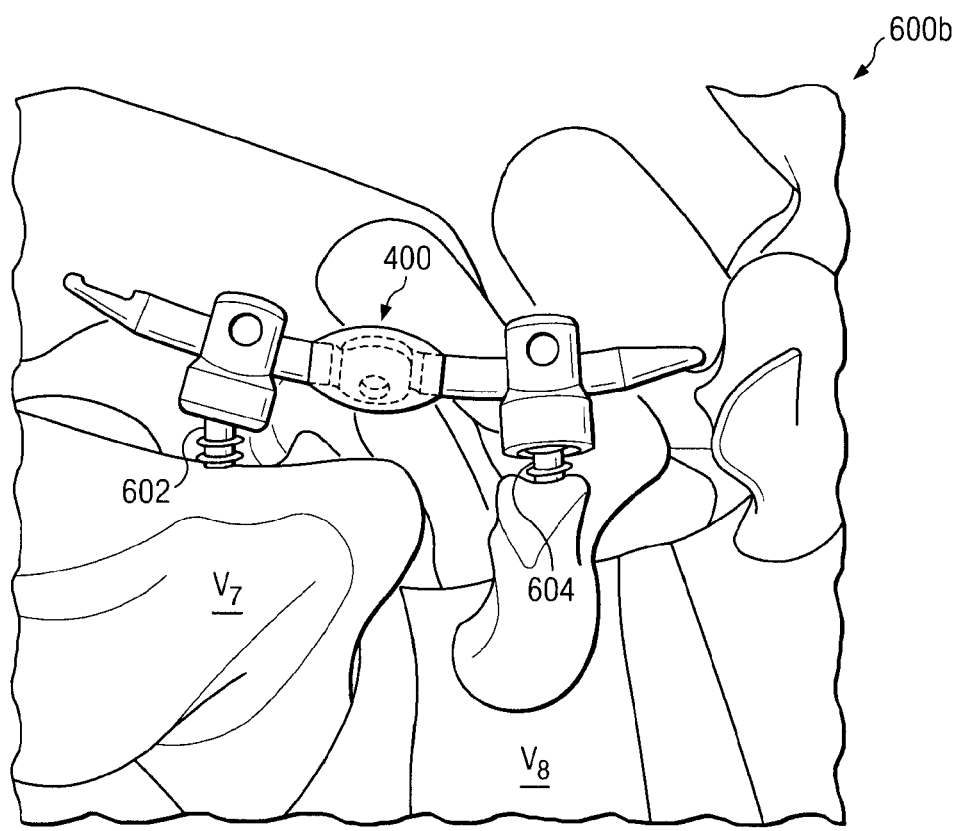
Figure 8:
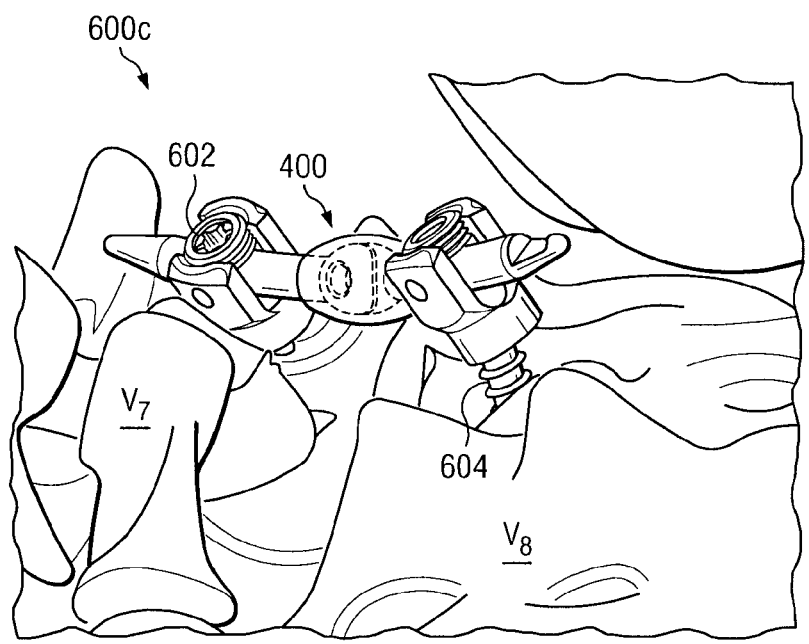

FIGS. 6-8 illustrate exemplary usages of the posterior device 400 as it is attached to the vertebrae of an animal body. For example, referring now to FIG. 6, shown therein is the posterior device 400 placed between the vertebrae V7, V8 by two multi-axial screws 602 and 604 according to one embodiment of the present invention. Further examples of attachment mechanisms that can be used are disclosed in U.S. Pat. Nos. 6,280,442, 5,891,145, 6,485,491, and 6,520,963, which are hereby incorporated by reference. FIGS. 7 and 8 illustrate perspective views of FIG. 6. from different angles to show the implementation of the posterior device 400 according to one embodiment of the invention.

Figure 9:
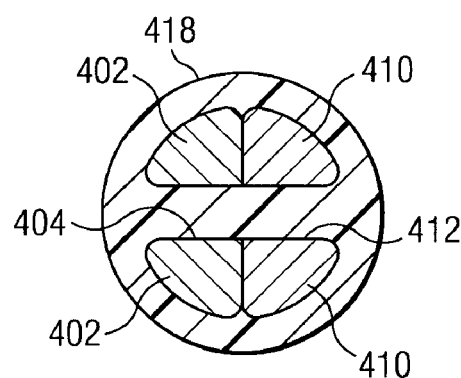
FIG. 9 illustrates a cross-sectional view of the posterior device of FIG. 5, taken along lines 9-9 in FIG. 5.

FIG. 9 shows one example of a cross-section of the posterior device of F*ig*. 5 taken along lines 9-9 in FIG. 5. In this example, as discussed above, elastic material is disposed through both openings 404, 412. In other examples, the connector 418 is hollow and not disposed through openings 404, 412.

Although only a few exemplary embodiments of this invention have been described above in details, those skilled in the art will readily appreciate that many modifications are possible in the exemplary embodiments without materially departing from the novel teachings and advantages of this invention. Also, features illustrated and discussed above with respect to some embodiments can be combined with features illustrated and discussed above with respect to other embodiments. For example, attachment mechanisms secured to a spinal process can alternatively be secured to a pedicle or lamina, as desired. Accordingly, all such modifications and alternatives are intended to be included within the scope of the claimed invention.

We claim:

1. A surgical implant for replacing functions of a facet joint between adjacent vertebrae, the surgical implant comprising:
   a first biocompatible attachment device for attaching to a first pedicle of a superior vertebrae;
   a second biocompatible attachment device for attaching to a second pedicle of an inferior vertebrae; and
   a flexible member attached to the first and second biocompatible attachment devices configured in a manner to allow motion at the facet joint;
   wherein the first and second biocompatible attachment devices are positioned, and the flexible member is adapted, so that the surgical implant applies a distracting force between the superior and inferior vertebrae sufficient for maintaining the first and second pedicles at a spaced-apart distance,
   wherein the flexible member includes:
      a first component comprising: an elongated body and a first joint element having a first opening;
      a second component comprising: an elongated body and a second joint element having a second opening wherein the second joint element is coupled with the first joint element;
      an elastic material disposed through both the first and second openings in a manner that dynamically secures the first and second components together and elastically flexes in a manner that permits relative movement between the first and second components; and
      a connector covering the first joint element and the second joint element, wherein the connector comprises the elastic material.

2. The posterior device of claim 1 wherein the first component further comprises a pointed tip adapted for percutaneous insertion of the posterior device.

3. The posterior device of claim 1 wherein the second component further comprises a pointed tip adapted for percutaneous insertion of the posterior device.

4. The posterior device of claim 1 wherein the connector is olive-shaped.

5. The posterior device of claim 1 wherein the first component and the second component are coupled at an angle of approximately 45° to the horizon to simulate the orientation of the facet joint.

6. The posterior device of claim 1 wherein the first component and the second component are coupled at an angle of approximately 60° to an axial plane and 20° to an frontal plane of a human body.

7. The posterior device of claim 1 wherein the first component and the second component are coupled at an angle of approximately 90° to an axial plane and 45° to an frontal plane of a human body.

8. A prosthetic device for replacing functions of a facet joint between adjacent vertebrae, the prosthetic device comprising:
   one or more flexible posterior devices configured to replace main functions of the facet joint, having a first biocompatible attachment device configured to attach to a first transverse process, and a second biocompatible attachment device configured to attach to a second transverse process, and wherein the one or more flexible posterior devices includes a joint component positioned between the first and second biocompatible attachment devices,
   wherein the one or more flexible posterior devices comprises:
   a first elongated body; and
   a second elongated body,
   wherein the joint component includes:
      a first element associated with the first elongated body, the first element having a first opening, and a second element associated with the second elongated body, the second element having a second opening, wherein the second element is coupled with the first element by an elastic material disposed in both the first and second openings; and a connector covering the first element and the second element wherein the connector comprises the elastic material.

9. The posterior device of claim 8 wherein the first elongated body further comprises a pointed tip adapted for percutaneous insertion of the posterior device.

10. The posterior device of claim 8 wherein the second elongated body further comprises a pointed tip adapted for percutaneous insertion of the posterior device.

11. The posterior device of claim 8 wherein the connector is olive-shaped.

12. The posterior device of claim 8 wherein the first elongated body and the second elongated body are coupled at an angle of approximately 45° to the horizon to simulate the orientation of the facet joint.

13. The posterior device of claim 8 wherein the first elongated body and the second elongated body are coupled at an angle of approximately 60° to an axial plane and 20° to an frontal plane of a human body.

14. The posterior device of claim 8 wherein the first elongated body and the second elongated body are coupled at an angle of approximately 90° to an axial plane and 45° to an frontal plane of a human body.

15. A surgical implant for replacing functions of a facet joint between adjacent vertebrae, the surgical implant comprising:

a first biocompatible attachment device for attaching to a first pedicle of a superior vertebrae;

a second biocompatible attachment device for attaching to a second pedicle of an inferior vertebrae; and a flexible member attached to the first and second biocompatible attachment devices configured in a manner to allow motion at the facet joint;

wherein the first and second biocompatible attachment devices are positioned, and the flexible member is adapted, so that the surgical implant applies a biasing distracting force between the superior and inferior vertebrae sufficient for maintaining the first and second pedicles at a spaced-apart distance, wherein the flexible member includes:

a first component comprising: an elongated body and a first joint element having a first opening;

a second component comprising: an elongated body and a second joint element having a second opening wherein the second joint element is coupled with the first joint element;

an elastic material that flexes to impart flexibility to the flexible member, the elastic material being disposed through both the first and second openings in a manner that dynamically secures the first and second components together and elastically flexes in a manner that permits relative movement between the first and second components and the superior and inferior vertebrae; and a connector covering the first joint element and the second joint element, wherein the connector comprises the elastic material.

* * * * *